United States Patent
Hommeltoft

(10) Patent No.: US 9,314,785 B1
(45) Date of Patent: Apr. 19, 2016

(54) KETONIZATION PROCESS USING OXIDATIVE CATALYST REGENERATION

(71) Applicant: Sven Ivar Hommeltoft, Pleasant Hill, CA (US)

(72) Inventor: Sven Ivar Hommeltoft, Pleasant Hill, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 2 days.

(21) Appl. No.: 14/540,723

(22) Filed: Nov. 13, 2014

(51) Int. Cl.
| | | |
|---|---|---|
| *B01J 38/66* | (2006.01) | |
| *B01J 38/06* | (2006.01) | |
| *C07C 45/48* | (2006.01) | |
| *B01J 21/04* | (2006.01) | |
| *B01J 21/20* | (2006.01) | |
| *B01J 38/04* | (2006.01) | |

(52) U.S. Cl.
CPC ........ *B01J 38/06* (2013.01); *B01J 21/04* (2013.01); *B01J 21/20* (2013.01); *B01J 38/04* (2013.01); *C07C 45/48* (2013.01)

(58) Field of Classification Search
CPC .................................................... B01J 38/66
USPC ................................................... 502/26
See application file for complete search history.

(56) References Cited

U.S. PATENT DOCUMENTS

| | | |
|---|---|---|
| 3,558,733 A | 1/1971 | Myers |
| 4,183,823 A | 1/1980 | George |
| 4,205,194 A | 5/1980 | Mitchell, III et al. |
| 4,377,495 A | 3/1983 | Tse |
| 4,724,271 A | 2/1988 | Martindale et al. |
| 4,780,195 A | 10/1988 | Miller |
| 4,795,726 A | 1/1989 | Schaper et al. |
| 5,075,268 A | 12/1991 | Kurashige et al. |
| 5,686,648 A | 11/1997 | Burzynski et al. |
| 2012/0149549 A1 | 6/2012 | Boeing et al. |
| 2012/0316093 A1 | 12/2012 | Zhan et al. |

*Primary Examiner* — Edward Johnson
(74) *Attorney, Agent, or Firm* — Steve H. Roth; Susan M. Abernathy

(57) ABSTRACT

Processes for fatty acid ketonization and alcohol dehydration, wherein an alumina catalyst disposed in, or removed from, a reaction zone may be regenerated by contacting the catalyst with steam during or after a coke oxidizing step. In an embodiment, such processes may provide $C_2$-$C_{43}$ alkenes. In another embodiment, such processes may provide $C_{11}$-$C_{43}$ ketones, which can be deoxygenated to give saturated hydrocarbons, unsaturated hydrocarbons, and mixtures thereof. Base oils and transportation fuels may be produced via such processes.

22 Claims, No Drawings

KETONIZATION PROCESS USING OXIDATIVE CATALYST REGENERATION

TECHNICAL FIELD

This disclosure relates to ketonization processes using oxidative catalyst regeneration.

BACKGROUND

There is a need for ketonization processes using oxidative catalyst regeneration for the efficient production of hydrocarbon base oils from biomass, fatty acids or their derivatives.

SUMMARY

In an embodiment there is provided a process comprising contacting a reactant with a catalyst in a reaction zone under reaction conditions to provide a product; after interrupting the prior step, contacting the catalyst with a flushing gas to remove the reactant and the product from the catalyst; contacting the catalyst with an oxidizing gas to remove coke from the catalyst; and contacting the catalyst with steam to provide regenerated catalyst, wherein the reaction zone is selected from the group consisting of a ketonization zone and an alcohol dehydration zone.

In another embodiment there is provided a process comprising contacting a catalyst with a flushing gas in a reaction zone selected from the group consisting of a ketonization zone and an alcohol dehydration zone; contacting the catalyst with an oxidizing gas to remove coke from the catalyst; and contacting the catalyst with steam to provide regenerated catalyst, wherein the catalyst consists essentially of alumina.

In a further embodiment there is provided a process comprising contacting a reactant with a catalyst in a ketonization zone under ketonization conditions to provide a product; after interrupting the prior step, contacting the catalyst with a flushing gas to remove the reactant and the product from the catalyst; after the step of contacting the catalyst with the flushing gas, contacting the catalyst with an oxidizing gas to remove coke from the catalyst; after or during the step of contacting the catalyst with the oxidizing gas, contacting the catalyst with steam to provide regenerated catalyst; and purging steam from the regenerated catalyst, wherein the catalyst comprises alumina, the reactant is selected from the group consisting of a $C_6$-$C_{22}$ fatty acid, a $C_6$-$C_{22}$ fatty acid derivative, and combinations thereof, and the product comprises a $C_{11}$-$C_{43}$ ketone.

DETAILED DESCRIPTION

Alumina catalysts that have become passivated, e.g., due to processing fatty acids to ketones, may be regenerated by steam treatment in conjunction with oxidative calcination, according to processes disclosed herein, to provide regenerated catalyst. In an embodiment, such regenerated alumina catalyst may have catalytic activity levels, as measured by fatty acid to ketone conversion, even greater than the catalytic activity of fresh alumina catalyst that has not undergone steam treatment. In an embodiment, processes as disclosed herein may include purging steam from steam-treated catalyst prior to the introduction of feed to the regenerated catalyst.

Catalysts for Ketonization and Alcohol Dehydration

In an embodiment, a suitable catalyst for ketonization or alcohol dehydration may comprise alumina. In an embodiment, the catalyst may comprise at least 95 wt %, at least 99 wt %, or at least 99.5 wt % alumina. In an embodiment, the fresh catalyst may be calcined at a temperature in the range from 700 to 1100° F. for a time period of 0.5 to 24 hours prior to contacting the catalyst with a reactant. In an embodiment, the fresh catalyst may be calcined in the presence of steam. In an embodiment, the catalyst may comprise gamma alumina. In an embodiment, the catalyst may consist essentially of alumina.

In an embodiment, the surface area of the alumina catalyst for ketonization or alcohol dehydration may be in the range from 15 to 500 $m^2$/g of catalyst, or from 50 to 400 $m^2$/g of catalyst, or from 100 to 250 $m^2$/g of catalyst. In an embodiment, an alumina catalyst useful in processes as disclosed herein may have various shapes including, for example, granules, pellets, spheres, extrudates, and the like. The alumina catalyst may be disposed within a ketonization zone or an alcohol dehydration zone. A ketonization zone or an alcohol dehydration zone is not limited to any particular reactor type. For example, a ketonization zone or an alcohol dehydration zone may use a fixed-, fluidized-, or moving bed reactor.

Over time, the catalyst may passivate and lose activity. The rate of passivation may vary according to the nature of the feedstock comprising the reactant and the operating conditions. In an embodiment, using substantially pure fatty acid(s) feedstocks the passivation rate may be in the range from 1 to 5° F. per day for conversion levels in the 50 to 80% range (for higher conversion levels and more challenging feedstocks the passivation rate may be higher than the stated range). The alumina catalyst is thermally stable, so it may be possible to compensate for catalyst passivation by increasing the reactor temperature; however, at very high temperatures the products may undergo cracking reactions, so there is a limit to how much the temperature can be raised without losing selectivity.

Accordingly, there is a need for the effective regeneration of passivated catalyst to allow for the efficient operation of alumina catalyzed processes as disclosed herein. An alumina catalyst that has become passivated to varying degrees may be regenerated, for example, as described hereinbelow.

Catalyst Regeneration

Processes as disclosed herein may involve contacting a reactant with an alumina catalyst in a reaction zone under reaction conditions to provide at least one product. It is to understood that the terms "reactant" and "product" may each be used herein to include a mixture comprising more than one chemical species, e.g., having different numbers of carbon atoms.

In an embodiment, a reactant may be fed to the reaction zone to provide a product, wherein the reaction zone may comprise a ketonization zone. The reactant fed to the ketonization zone may comprise a $C_6$-$C_{22}$ fatty acid, a $C_6$-$C_{22}$ fatty acid derivative, and combinations thereof. The reactant may be fed to the ketonization zone under ketonization conditions, and the product from the ketonization zone may comprise a $C_{11}$-$C_{43}$ ketone and combinations thereof. In an embodiment, product(s) provided by ketonization processes as disclosed herein may comprise saturated aliphatic ketones, unsaturated aliphatic ketones, and combinations thereof.

In a sub-embodiment, a reactant fed to the ketonization zone to provide a ketone product may comprise a first fatty acid and a second fatty acid, according to the following Scheme 1:

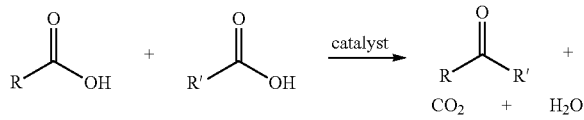

wherein R and R' may be the same or different, and wherein R and R' are independently selected from $C_5$-$C_{21}$ alkyl and $C_5$-$C_{21}$ alkenyl. Suitable catalysts for ketonization are described, for example, hereinabove. Suitable conditions for ketonization are described, for example, hereinbelow.

In another embodiment, the reaction zone may comprise an alcohol dehydration zone. In an embodiment, a reactant fed to the alcohol dehydration zone may comprise a $C_2$-$C_{43}$ alcohol, and combinations thereof. The reactant may be fed to the alcohol dehydration zone under alcohol dehydration conditions, and the product from the alcohol dehydration zone may comprise a $C_2$-$C_{43}$ alkene, and combinations thereof.

Following use in a ketonization or alcohol dehydration zone, the catalyst may be passivated and lose activity, at which time the catalyst may be regenerated, e.g., as described hereinbelow. After interrupting the feed of reactant(s) to the reaction zone/catalyst, processes as disclosed herein may further involve contacting the catalyst with a flushing gas to remove any unconverted reactant, product, by-products, and the like from the catalyst. In an embodiment, the flushing gas may comprise a gas selected from the group consisting of nitrogen, steam, carbon dioxide, and combinations thereof. In another embodiment, the flushing gas may comprise a noble gas, such as helium (He), neon (Ne), argon (Ar), and combinations thereof.

After flushing the catalyst, e.g., as described hereinabove, the catalyst may be contacted with an oxidizing gas to remove coke from the catalyst. For example, the catalyst may be contacted with the oxidizing gas under conditions suitable for the controlled burning of coke from the catalyst. In an embodiment, the oxidizing gas may comprise oxygen in the range from 0.5 to 21 vol %. The oxidizing gas may further comprise a diluent gas such as nitrogen, steam, carbon dioxide, and combinations thereof.

Processes as disclosed herein may still further involve contacting the catalyst with steam to provide regenerated catalyst. In an embodiment, the step of contacting the catalyst with steam for catalyst regeneration may be performed after at least a portion of the coke has been removed from the catalyst, e.g., after or during the step of contacting the catalyst with the oxidizing gas. In an embodiment, the step of contacting the catalyst with steam may be performed at a temperature in the range from 300 to 1000° F. (149 to 538° C.), or from 500 to 850° F. (260 to 454° C.). Without being bound by theory, contacting the catalyst with steam may restore surface hydroxyl groups on the alumina.

In an embodiment, the step of contacting the catalyst with the oxidizing gas and the step of contacting the catalyst with steam may be performed in situ in the reaction zone. In an embodiment, the catalyst regeneration may be performed at substantially ambient pressure.

Processes as disclosed herein may yet further involve purging steam from the regenerated catalyst. In an embodiment, at least some portion of the steam may be purged from the regenerated catalyst. In another embodiment, the steam may be entirely removed from the regenerated catalyst such that the catalyst is at least substantially free of moisture. Notwithstanding the fact that water is formed during reactions in the reaction zone, and without being bound by theory, Applicant has observed that the presence of even small to moderate amounts of water in the ketonization zone may negatively impact the reaction rate and thus the conversion of fatty acids to ketone product(s).

In an embodiment, steam may be purged from the regenerated catalyst using a stream of dry gas, such as nitrogen. In another embodiment, steam may be purged from the regenerated catalyst by feeding the reactant to the reaction zone. In a sub-embodiment, the reactant may be a fatty acid component of a feedstock. In an embodiment, the feedstock may comprise at least 95 wt % fatty acids or at least 99 wt % fatty acids.

In an embodiment, the oxidizing gas may comprise oxygen and a diluent gas. In a sub-embodiment, the flushing gas may comprise steam, the oxidizing gas may further comprise steam as a diluent gas, and the step of contacting the catalyst with steam may be performed during the step of contacting the catalyst with the oxidizing gas, i.e., in the presence of the oxidizing gas. In another embodiment, the step of contacting the catalyst with steam may be performed after the step of contacting the catalyst with the oxidizing gas, i.e., in the absence of the oxidizing gas.

In an embodiment, one or more steps of the process, such as the step of contacting the catalyst with the oxidizing gas and/or the step of contacting the catalyst with steam, may be performed while the catalyst is disposed in a fixed bed. In another embodiment, each step of the process may be performed while the catalyst is disposed in a fixed bed. In an embodiment, the entire process including the ketonization reaction and the catalyst regeneration steps may be performed in situ in the reaction zone.

In another embodiment, the step of contacting a reactant with the catalyst may be performed in a reaction zone, and the catalyst may be subsequently removed from the reaction zone to a separate vessel for catalyst regeneration. That is to say, in an embodiment the reaction (e.g., ketonization or alcohol dehydration) and catalyst regeneration may be performed in different reactors or vessels. In an embodiment, during the step of contacting a reactant with the catalyst, the catalyst may be disposed in a fluidized bed or moving bed, i.e., the reaction zone may comprise a fluidized bed or moving bed of the catalyst, e.g., alumina. For catalyst regeneration, the passivated catalyst may be withdrawn from the reaction zone and injected into a regenerator vessel. As a non-limiting example, a ketonization zone may comprise a fluidized bed of alumina catalyst or a moving bed of alumina catalyst, and the passivated catalyst may be continuously or periodically withdrawn to a regenerator vessel for catalyst regeneration, e.g., via coke oxidation and steam treatment as described hereinabove.

During the coke burning stage, the temperature of the catalyst may be controlled by varying the oxygen concentration in the oxidizing gas, e.g., by the addition of diluent gas to the oxidizing gas. In an embodiment, the step of contacting the catalyst with the oxidizing gas may be conducted at a temperature 900° F. (482° C.). Due to the thermal stability of the alumina catalyst, in an embodiment the temperature of the catalyst during the coke oxidizing stage may be limited only by the heat tolerance of the reactor or other vessel containing the catalyst.

In an embodiment, the step of contacting the catalyst with the oxidizing gas may be performed in the reaction zone. During the step of contacting the catalyst with the oxidizing gas, the removal of coke from the catalyst may be monitored by comparing an inlet oxygen concentration with an outlet oxygen concentration and/or by monitoring the outlet carbon dioxide concentration.

In an embodiment, the step of contacting the catalyst with steam may comprise pre-heating steam and thereafter injecting the steam into a vessel containing the catalyst during catalyst regeneration. In a sub-embodiment, liquid water or steam may be combined with another gas, and the mixture may be pre-heated before injecting the gaseous mixture into the vessel containing the catalyst. In an embodiment, the step of contacting the catalyst with steam may be performed in the reaction zone.

In an embodiment, an alumina catalyst that has been regenerated as disclosed herein may have catalytic activity at least as great as that of a fresh sample of the alumina catalyst. After the catalyst regeneration process, a fatty acid reactant or an alcohol reactant may be contacted with the regenerated catalyst in a ketonization zone or an alcohol dehydration zone to provide a ketone product or an alkene product, respectively. Exemplary feedstocks and reactants for ketonization and alcohol dehydration reactions are disclosed hereinbelow.

In a sub-embodiment of a process for alumina catalyst regeneration, the feed to the catalyst may be stopped and any product, residual reactant or other feed constituent(s) may be flushed from the passivated catalyst by a stream of hot steam, wherein the catalyst may be disposed in situ in the reaction zone. Thereafter, the flushed catalyst may be contacted with oxidizing gas to remove coke from the catalyst. Thereafter the catalyst may be contacted with steam to provide regenerated catalyst. In a sub-embodiment, the feedstock may be passed through the catalyst in the reaction zone after the steam treatment so as to not only cool the reaction zone, e.g., to reaction conditions, but also to flush the steam from the catalyst/reaction zone. In another sub-embodiment, the passage of steam may be continued so as to cool the reaction zone to reaction conditions before resuming the feed.

Fatty Acid Ketonization

A ketone product may be prepared by ketonization of a reactant comprising a first fatty acid and a second fatty acid according to the following scheme (Scheme 1), wherein R and R' are saturated or unsaturated aliphatic groups, and wherein R and R' may be the same or different. As a non-limiting example, R and R' may be independently selected from $C_5$-$C_{21}$ alkyl and $C_5$-$C_{21}$ alkenyl.

Scheme 1:

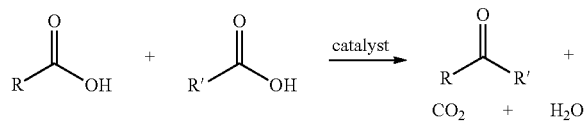

In an embodiment, ketonization may also be known as ketonic decarboxylation or fatty acid decarboxylation-coupling.

In an embodiment, feedstocks for ketonization as disclosed herein may be derived from a triglyceride-containing biomass source such as oils or fats from plants and/or animals. In an embodiment, the fatty acid feedstock may be derived from other, non-biomass, sources (e.g., Fischer-Tropsch synthesis). Such alternatively derived fatty acids may be mixed or blended with biomass derived fatty acids prior to ketonization, e.g., to alleviate logistical and/or supply related issues involving biomass.

In an embodiment, feedstocks for ketonization may comprise at least one fatty acid reactant or a mixture of fatty acid reactants. In an embodiment, reactants for ketonization may comprise $C_6$-$C_{22}$ fatty acids and/or $C_6$-$C_{22}$ fatty acid derivatives. In an embodiment, such fatty acid derivatives may include $C_6$-$C_{22}$ fatty acid mono-, di-, and triglycerides, $C_6$-$C_{22}$ acyl halides, and $C_6$-$C_{22}$ salts of fatty acids. In an embodiment, feedstocks for ketonization may comprise at least 95 wt % fatty acids or at least 99 wt % fatty acids.

In an embodiment, reactants for ketonization may be derived from one or more triglyceride-containing vegetable oils such as, but not limited to, coconut oil, corn oil, linseed oil, olive oil, palm oil, palm kernel oil, rapeseed oil, safflower oil, soybean oil, sunflower oil, and the like. Additional or alternative sources of triglycerides, which can be hydrolyzed to yield fatty acids, include, but are not limited to, algae, animal tallow, and zooplankton.

In an embodiment, reactants for ketonization may include, without limitation, $C_8$-$C_{22}$ fatty acids, and combinations thereof. Examples of suitable saturated fatty acids may include, without limitation, caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), eicosanoic acid ($C_{20}$). Examples of unsaturated acids may include, without limitation, palmitoleic acid, oleic acid, and linoleic acid. Reactants for ketonization may further include, without limitation, palm kernel oil, palm oil, coconut oil, soy bean oil, rape seed oil, poultry fat, beef tallow, and their respective fatty acid constituents, and combinations thereof.

In some aspects, wherein the above-mentioned hydrolyzed triglyceride sources contain mixtures of saturated fatty acids, mono-unsaturated fatty acids, and polyunsaturated fatty acids, one or more techniques may be employed to isolate, concentrate, or otherwise separate one or more types of fatty acids from one or more other types of fatty acids in the mixture (see, e.g., U.S. Patent Application Publication No. 2009/0285728).

Prior to contacting the reactant with the catalyst in the ketonization zone, the catalyst may be calcined. In an embodiment, the step of calcining the catalyst may be performed in the presence of steam. In an embodiment, the step of calcining the catalyst may be performed at a temperature in the range from 400 to 600° C., or from 450 to 500° C., for a time period in the range from 0.5 to 10 hours, or from 1 to 2 hours.

In an embodiment, a suitable catalyst for fatty acid ketonization may comprise alumina. In an embodiment, the catalyst may comprise substantially pure gamma alumina. In an embodiment, the catalyst may consist essentially of alumina.

Suitable ketonization conditions may include a temperature in the range from 100° C. to 500° C., or from 300° C. to 450° C.; a pressure in the range from 0.5 to 100 psi, or from 5 to 30 psi; and a liquid hourly space velocity (LHSV) in the range from 0.1 to 50 If, or from 0.5 to 10 h$^{-1}$. In an embodiment, the partial pressure of the fatty acid in the ketonization zone may be maintained in the range of 0.1 to 30 psi. The ketonization process can be carried out in batch or continuous mode, with recycling of unconsumed starting materials if required.

In an embodiment, the decarboxylation reaction may be conducted in the presence of at least one gaseous- or liquid feedstock diluent. In an embodiment, the ketonization reaction may be carried out while the fatty acid is maintained in the vapor phase. Conditions for fatty acid ketonization are disclosed in commonly assigned U.S. patent application Ser. No. 13/486,097, filed Jun. 1, 2012, entitled Process for producing ketones from fatty acids.

Ketones derived by the above described process can be separated from by-products (such as oligomeric or polymeric species and low molecular weight "fragments" from the fatty acid chains) by distillation. For example, the crude reaction product can be subjected to a distillation-separation at atmospheric or reduced pressure through a packed distillation column. In an embodiment, the ketonization product may be a wax under ambient conditions.

Ketones produced as disclosed herein may be separated from other materials and subjected to hydroprocessing as disclosed hereinbelow to provide a range of products for use as, or in, lubricants and liquid fuels. As an example, processes disclosed herein may involve one or more of the following:

distilling, flash distillation, hydrocracking, hydroisomerization dewaxing, hydrofinishing, and combinations thereof.

Alcohol Dehydration

In an embodiment, a process for alcohol dehydration may be performed by contacting an alcohol reactant with a suitable catalyst under alcohol dehydration conditions in an alcohol dehydration zone. In an embodiment, such alcohol reactants may be obtained from Fischer-Tropsch (F-T) condensate. In an embodiment, alcohol reactants for alcohol dehydration processes disclosed herein may be predominantly $C_2$-$C_{20}$ primary alcohols.

In an embodiment, a suitable catalyst for alcohol dehydration may comprise alumina. In an embodiment, the catalyst may comprise substantially pure gamma alumina. In an embodiment, the catalyst may consist essentially of alumina.

Suitable conditions for alcohol dehydration in the presence of an alumina catalyst may include a temperature in the range from 100° C. to 500° C., or from 200° C. to 400° C.; a pressure in the range from 1 to 2000 psi, or from atmospheric pressure to 100 psi; and a liquid hourly space velocity (LHSV) of from 0.1 to 50 If, or from 1 to 5 h$^{-1}$. In an embodiment, the alcohol dehydration process can be carried out in batch or continuous mode, with recycling of unconsumed starting materials if required.

Distilling

In an embodiment, the step of distilling employs a distillation column to separate the desired product(s), e.g., ketones, from by-products (such as oligomeric or polymeric species and low molecular weight "fragments" from the reactant). In an embodiment, the step of distilling may employ flash distillation or partial condensation techniques to remove by-products including at least low molecular weight "fragments".

Those of skill in the art will recognize that there is some flexibility in characterizing the high and low boiling fractions, and that the products may be obtained from "cuts" at various temperature ranges.

Hydrocracking

Hydrocracking is generally accomplished by contacting, in a hydrocracking reactor or hydrocracking zone, the feedstock (e.g., ketone products) to be treated with a suitable hydrocracking catalyst under conditions of elevated temperature and pressure. Hydrocracking reactions may decrease the overall molecular weight of the heavy feedstock to yield upgraded (that is, higher value) products including transportation fuels (e.g., diesel fuel), kerosene, and naphtha. These upgraded products that are converted in the hydrocracking reaction zone are typically separated from the total hydrocracker effluent as lower boiling fractions, using one or more separation and/or distillation operations. A remaining higher boiling fraction, containing heavy waxy products (referred to herein as a "heavy hydrocarbon intermediate" or a "heavy waxy oil") suitable for upgrading to lubricating base oils by hydroisomerization to improve its cold flow properties, is typically isolated in the fractionators. Such heavy waxy oil may have a boiling range of approximately 343° C. to 704° C.

The temperature in the hydrocracking zone may be within the range from 260° C. to 482° C., typically from 316° C. to 427° C., and often from 343° C. to 399° C. A total pressure above 1000 psig (6.89 MPa) is used in the hydrocracking zone. For example, the total pressure can be above 1500 psig (10.34 MPa), or above 2000 psig (13.79 MPa). Although greater maximum pressures have been reported in the literature and may be operable, the maximum practical total pressure generally will not exceed 3000 psig (20.68 MPa). In an embodiment, more severe hydrocracking conditions such as higher temperature or pressure will result in an original base oil product with a higher viscosity index.

The LHSV for hydrocracking generally falls within the range from 0.1 to 50 If, typically from 0.2 to 10 If, and often from 0.5 to 5 h$^{-1}$. The supply of hydrogen (both make-up and recycle) is preferably in excess of the stoichiometric amount needed to crack the target molecules and generally falls within the range from 500 to 10000 standard cubic feet (SCF)/barrel, typically from 1000 to 5000 SCF/barrel. Note that a feed rate of 10000 SCF/barrel is equivalent to 1781 L H$_2$/L feed. In general, hydrocracking conditions are sufficient to convert the ketones to hydrocarbons.

The catalysts used in the hydrocracking zone are composed of natural and synthetic materials having hydrogenation and dehydrogenation activity and cracking activity. These catalysts are well known in the art and are pre-selected to crack the target molecules and produce the desired product slate. Exemplary commercial cracking catalysts generally contain a support consisting of alumina, silica, silica-alumina composites, silica-alumina-zirconia composites, silica-alumina-titania composites, acid treated clays, crystalline aluminosilicate zeolitic molecular sieve (e.g., zeolite A, faujasite-Y, zeolite beta), and various combinations of the above. The hydrogenation/dehydrogenation components generally consist of a metal or metal compound of Group VIII or Group VIB of the Periodic Table of the Elements. Metals and their compounds such as, for example, Co, Ni, Mo, W, Pt, Pd and combinations thereof are known hydrogenation components of hydrocracking catalysts.

Hydroisomerization Dewaxing

Heavy intermediate products are characterized by high pour points and high cloud points.

In order to prepare commercially useful lubricating base oils from heavy intermediate products, the pour point and cloud point must be lowered without compromising the desired viscosity characteristics. Hydroisomerization dewaxing is intended to improve the cold flow properties of the heavy intermediate products by the selective addition of branching into the molecular structure. Hydroisomerization dewaxing ideally will achieve high conversion levels of the waxy oil to non-waxy isoparaffins while at the same time minimizing cracking.

Hydroisomerization dewaxing is achieved by contacting a feed with a hydroisomerization dewaxing catalyst in a hydroisomerization zone under hydroisomerization dewaxing conditions. The hydroisomerization catalyst preferably may comprise a shape selective intermediate pore size molecular sieve, a noble metal hydrogenation component, and at least a refractory oxide support. The shape selective intermediate pore size molecular sieve is preferably selected from the group consisting of SAPO-11, SAPO-31, SAPO-41, SM-3, SM-7, ZSM-22, ZSM-23, ZSM-35, ZSM-48, ZSM-57, SSZ-32, ferrierite, and combinations thereof. SAPO-11, SM-3, SM-7, SSZ-32, ZSM-23, and combinations thereof are often used. The noble metal hydrogenation component can be Pt, Pd, or combinations thereof.

The hydroisomerization dewaxing conditions depend on the feed used, the hydroisomerization dewaxing catalyst, whether or not the catalyst is sulfided, the desired yield, and the desired properties of the product. In an embodiment, hydroisomerization dewaxing conditions may include temperatures of 260° C. to 413° C.; a total pressure of 15 to 3000 psig (0.10 to 20.68 MPa); a LHSV of 0.25 to 20 h$^{-1}$; and a hydrogen to feed ratio from 200 to 30000 SCF/barrel. In an embodiment, the hydrogen to feed ratio can be from 500 to 10000 SCF/barrel, in others from 1000 to 5000 SCF/barrel, and in still others from 2000 to 4000 SCF/barrel. Typically, hydrogen will be separated from the product and recycled to the hydroisomerization zone. Additional details of suitable hydroisomerization dewaxing processes are described in U.S. Pat. Nos. 5,135,638; 5,282,958; and 7,282,134.

Hydrofinishing

Hydrofinishing may be used as a step following hydroisomerization in processes as disclosed herein to make base oils with improved properties. Hydrofinishing is intended to improve the oxidation stability, UV stability, and appearance of the product by removing traces of olefins and color bodies. A general description of hydrofinishing may be found in U.S. Pat. Nos. 3,852,207 and 4,673,487. In one embodiment, the isomerized product from the hydroisomerization reactor passes directly to the hydrofinishing reactor.

As used in this disclosure, the term UV stability refers to the stability of the lubricating base oil when exposed to ultraviolet light and oxygen. Instability is indicated when the lubricating base oil forms a visible precipitate or darker color upon exposure to ultraviolet light and air which results in a cloudiness or floc in the product. Usually lubricating base oils prepared by hydrocracking followed by hydroisomerization require UV stabilization before they are suitable for use in the manufacture of commercial lubricating oils.

Processes as disclosed herein may further comprise blending saturated or unsaturated hydrocarbon products with a base oil selected from the group consisting of Group I base oils, Group II base oils, Group III base oils, and combinations thereof.

EXAMPLES

Example 1

Ketonization of Lauric Acid to Laurone Using Alumina Catalyst

The ketonization of lauric acid to laurone was catalyzed by an alumina catalyst operated in a fixed bed continuously fed reactor at ambient pressure, at a temperature range of 770-840° C., and with a feed rate that gave a liquid hourly space velocity (LHSV) of 0.62-0.64. The conversion rate of lauric acid to laurone was calculated based on the composition of the product as determined by GC analysis using an FID detector.

The freshly loaded new alumina catalyst was calcined in the reactor at 900° F. (482° C.) with a stream of dry nitrogen (2 volumes of nitrogen per volume of catalyst per minute) for 2 hours before the temperature was lowered to 770° F. (410° C.), nitrogen was turned off and the lauric acid feed was introduced. Product composition analysis showed that the fresh catalyst operating at 770° F., LHSV=0.62-0.64, gave a lauric acid conversion of 62-66%.

Example 2

Passivation of the Alumina Catalyst of Example 1

The reactor containing alumina catalyst as in Example 1 was kept operating for more than 500 hrs using gradually increasing temperature to compensate for gradually increasing catalyst passivation. After continuing operation for 500 hrs at gradually increasing temperature from 770° F. to 810° F. (410 to 432° C.), the conversion began to decrease in spite of the continued increase of reaction temperature and after 700 hrs the conversion rate was down to 50% in spite of a reactor temperature of around 820° F., indicating a significant degree of catalyst passivation.

Example 3

Alumina Catalyst Regeneration without Steam Treatment (Comparative)

The passivated catalyst from Example 2 was regenerated by oxidative calcination as follows. The lauric acid feed flow was stopped and nitrogen was passed through the reactor at a flow rate of 20 volumes of nitrogen per volume of catalyst per minute while increasing the temperature to 900° F. (482° C.). After 1 hr at 900° F. the gas was switched to 2% oxygen in nitrogen (oxidizing gas) at the same volumetric flow. These conditions were held for 3 days to ensure that coke was completely burned off. The catalyst was then cooled down to 770° F. (410° C.) in a stream of nitrogen before re-introducing the lauric acid feed.

The thus regenerated catalyst when operated at the same conditions as the fresh catalyst (770° F., LHSV=0.62-0.64) gave only about 45% conversion indicating that though much of the activity had been restored the regenerated catalyst only had about 70% of the activity of the fresh catalyst.

While not being bound by theory, the lower catalytic activity observed for the alumina regenerated using oxidizing gas without steam treatment (cf. fresh catalyst) may be caused by the loss of Al—OH groups from the catalyst surface during exposure of the alumina to dry gas at elevated temperatures.

Example 4

Alumina Catalyst Regeneration Using Steam Treatment after Oxidative Calcination

The catalyst from Examples 1-3 was used for further processing of lauric acid to laurone and the catalyst again became passivated, at which point the catalyst was regenerated by oxidative calcination under the same conditions as described in Example 3 except that the oxidative treatment was done for only about 15 hrs., after which time the flow of oxygen containing gas was shut off and the catalyst was treated with steam by feeding water (LHSV=0.6) together with nitrogen (2 volumes of nitrogen per volume of catalyst per minute) over the catalyst at 770° F. (410° C.) for 2 hrs before switching to feed.

The catalytic activity of the catalyst regenerated according to this Example 4 was once again assessed during processing lauric acid at 770° F. and LHSV=0.62-0.64, and in this Example 4 the conversion rate of lauric acid to laurone was 70%, indicating that the oxidatively calcined and steamed catalyst had about 5-10% higher activity as compared with fresh catalyst that had not been steam treated.

This shows that catalyst regeneration by oxidative calcination followed by steaming can fully restore the catalytic activity of an alumina catalyst used for ketonization of fatty acids.

While not being bound by theory, the higher catalytic activity observed for the alumina regenerated using oxidizing gas and steam treatment may be due to restoration of Al—OH groups on the catalyst surface by exposure of the alumina to steam.

Example 5

Alumina Catalyst Regeneration Using Steam Treatment During Oxidative Calcination Alumina catalyst that had become passivated following processing lauric acid to laurone (770° F. (410° C.), LHSV=0.62-0.64) was regenerated using steam treatment in conjunction with oxidative calcination as described in Example 4 except that in this Example 5 the steam treatment was performed before the end of the oxidative calcination, i.e., in the presence of oxygen containing gas. The activity of the catalyst regenerated according to this Example 5 was again assessed and found to be similar to that described in Example 4.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Additionally, chemical species including reactants and products designated by a numerical range of carbon atoms include any one or more of, or any combination of, or all of the chemical species within that range.

Any term, abbreviation or shorthand not defined is understood to have the ordinary meaning used by a person skilled in the art at the time the application is filed. The singular forms "a," "an," and "the," include plural references unless expressly and unequivocally limited to one instance. All publications, patents, and patent applications cited in this application are incorporated by reference herein in their entirety to the extent not inconsistent herewith.

Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A process comprising:
    a) contacting a reactant with a catalyst in a reaction zone under reaction conditions to provide a product;
    b) after interrupting step a), contacting the catalyst with a flushing gas to remove the reactant and the product from the catalyst;
    c) contacting the catalyst with an oxidizing gas to remove coke from the catalyst; and
    d) contacting the catalyst with steam to provide regenerated catalyst, wherein the reaction zone is selected from the group consisting of a ketonization zone and an alcohol dehydration zone.

2. The process according to claim 1, further comprising:
    e) purging steam from the regenerated catalyst.

3. The process according to claim 2, wherein step e) comprises feeding the reactant to the reaction zone.

4. The process according to claim 1, wherein:
    the reaction zone comprises said alcohol dehydration zone, and the reactant is selected from the group consisting of a $C_2$-$C_{43}$ alcohol, and combinations thereof.

5. The process according to claim 1, wherein:
    the reaction zone comprises said ketonization zone, and the reactant is selected from the group consisting of a $C_6$-$C_{22}$ fatty acid, a $C_6$-$C_{22}$ fatty acid derivative, and combinations thereof.

6. The process according to claim 1, wherein:
    the reactant comprises a first fatty acid and a second fatty acid, and the product comprises a ketone formed according to the following Scheme 1:

Scheme 1:

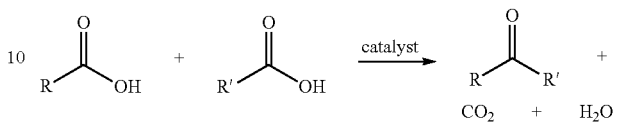

wherein R and R' are the same or different, and R and R' are independently selected from the group consisting of $C_5$-$C_{21}$ alkyl and $C_5$-$C_{21}$ alkenyl.

7. The process according to claim 1, wherein the catalyst consists essentially of alumina.

8. The process according to claim 1, wherein:
    the flushing gas comprises a gas selected from the group consisting of nitrogen, steam, carbon dioxide, and combinations thereof, and
    the oxidizing gas comprises oxygen in the range from 0.5 to 21 vol %.

9. The process according to claim 8, wherein:
    the flushing gas comprises steam,
    the oxidizing gas further comprises steam, and
    step d) is performed during step c).

10. The process according to claim 1, wherein the process is performed in situ in the reaction zone.

11. The process according to claim 1, wherein the reaction zone comprises a fluidized bed of the catalyst or a moving bed of the catalyst, and the process further comprises:
    f) prior to step b), injecting the catalyst into a regenerator vessel for regeneration of the catalyst according to steps b)-d), wherein step f) is performed continuously or periodically.

12. A process comprising:
    a) contacting a catalyst with a flushing gas in a reaction zone selected from the group consisting of a ketonization zone and an alcohol dehydration zone;
    b) contacting the catalyst with an oxidizing gas to remove coke from the catalyst; and
    c) contacting the catalyst with steam to provide regenerated catalyst, wherein the catalyst consists essentially of alumina.

13. The process according to claim 12, further comprising:
    d) purging steam from the regenerated catalyst.

14. The process according to claim 12, further comprising:
    e) feeding a reactant to the reaction zone to provide a product, wherein the reaction zone comprises said ketonization zone.

15. The process according to claim 14, wherein:
    the reactant is selected from the group consisting of a $C_6$-$C_{22}$ fatty acid, a $C_6$-$C_{22}$ fatty acid derivative, and combinations thereof, and
    the product comprises a $C_{11}$-$C_{43}$ ketone.

16. The process according to claim 14, wherein steps b) and c) are performed in situ in said ketonization zone.

17. The process according to claim 12, wherein step c) is performed after step b) in the absence of the oxidizing gas.

18. The process according to claim 12, wherein step c) is performed during step b) in the presence of the oxidizing gas.

19. A process comprising:
    a) contacting a reactant with a catalyst in a ketonization zone under ketonization conditions to provide a product;

b) after interrupting step a), contacting the catalyst with a flushing gas to remove the reactant and the product from the catalyst;
c) after step b), contacting the catalyst with an oxidizing gas to remove coke from the catalyst;
d) after or during step c), contacting the catalyst with steam to provide regenerated catalyst; and
e) purging steam from the regenerated catalyst, wherein:
the catalyst comprises alumina,
the reactant is selected from the group consisting of a $C_6$-$C_{22}$ fatty acid, a $C_6$-$C_{22}$ fatty acid derivative, and combinations thereof, and
the product comprises a $C_{11}$-$C_{43}$ ketone.

20. The process according to claim 19, wherein the ketonization zone comprises a fluidized bed of the catalyst or a moving bed of the catalyst, and the process further comprises:
f) prior to step b), injecting the catalyst into a regenerator vessel for regeneration of the catalyst according to steps b)-d), wherein step f) is performed continuously or periodically.

21. The process according to claim 19, further comprising:
g) contacting the reactant with the regenerated catalyst.

22. The process according to claim 19, wherein the catalyst consists essentially of alumina.

* * * * *